(12) United States Patent
Wu et al.

(10) Patent No.: US 9,002,436 B2
(45) Date of Patent: *Apr. 7, 2015

(54) METHOD AND SYSTEM FOR ABLATION CATHETER AND CIRCUMFERENTIAL MAPPING CATHETER TRACKING IN FLUOROSCOPIC IMAGES

(71) Applicant: Siemens Aktiengesellschaft, Munich (DE)

(72) Inventors: Wen Wu, East Windsor, NJ (US); Terrence Chen, Princeton, NJ (US); Norbert Strobel, Heroldsbach (DE); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 114 days.

This patent is subject to a terminal disclaimer.

(21) Appl. No.: 13/622,404

(22) Filed: Sep. 19, 2012

(65) Prior Publication Data

US 2013/0072773 A1 Mar. 21, 2013

Related U.S. Application Data

(60) Provisional application No. 61/536,102, filed on Sep. 19, 2011.

(51) Int. Cl.
*A61B 5/05* (2006.01)
*G06K 9/62* (2006.01)
(Continued)

(52) U.S. Cl.
CPC ............... *G06K 9/6297* (2013.01); *A61B 6/12* (2013.01); *A61B 6/487* (2013.01); *A61B 18/1492* (2013.01); *A61B 2018/00577* (2013.01); *A61B 2019/5238* (2013.01); *A61B 2018/00315* (2013.01); *A61B 19/5244* (2013.01); *A61B 2019/502* (2013.01); *A61B 2019/5265* (2013.01); *G06T 7/204* (2013.01); *G06T 7/208* (2013.01); *G06T2207/10121* (2013.01); *G06T 2207/20081* (2013.01); *G06T 2207/20101* (2013.01); *G06T 2207/30021* (2013.01); *G06K 2209/057* (2013.01)

(58) Field of Classification Search
CPC ...... A61B 6/12; A61B 19/5244; A61B 6/487; G06T 7/204; G06T 7/208; G06T 2207/10121; G06T 2207/20081; G06T 2207/20101; G06T 2207/30021; G06K 9/6297; G06K 2209/057
USPC ........................................................ 600/424
See application file for complete search history.

(56) References Cited

U.S. PATENT DOCUMENTS

| 7,792,342 | B2 | 9/2010 | Barbu et al. | |
| 2003/0014034 | A1* | 1/2003 | Strobel | 604/407 |

(Continued)

*Primary Examiner* — Jonathan Cwern
*Assistant Examiner* — Amelie R Gillman

(57) ABSTRACT

A method and system for tracking an ablation catheter and a circumferential mapping catheter in a fluoroscopic image sequence is disclosed. Catheter electrode models for the ablation catheter and the circumferential mapping catheter are initialized in a first frame of a fluoroscopic image sequence based on user inputs. The catheter electrode models for the ablation catheter and the circumferential mapping catheter are then tracked in each remaining frame of the fluoroscopic image sequence. In each remaining frame, candidates of catheter landmarks such as the catheter tip, electrodes and body points are detected for the ablation catheter and the circumferential mapping catheter, tracking hypotheses for the catheter electrode models are generated, and for each of the ablation catheter and the circumferential mapping catheter, the catheter electrode model having the highest probability score is selected from the generated tracking hypotheses.

30 Claims, 7 Drawing Sheets

(51) Int. Cl.
    *A61B 6/12* (2006.01)
    *G06T 7/20* (2006.01)
    *A61B 6/00* (2006.01)
    *A61B 18/14* (2006.01)
    *A61B 18/00* (2006.01)
    *A61B 19/00* (2006.01)

(56) References Cited

U.S. PATENT DOCUMENTS

2003/0235337 A1* 12/2003 Paragios et al. ............... 382/215
2005/0152617 A1* 7/2005 Roche et al. ................... 382/294
2007/0270692 A1* 11/2007 Barbu et al. ................... 600/431
2008/0080754 A1 4/2008 Barbu et al.
2008/0139930 A1* 6/2008 Weese et al. ................... 600/424
2008/0317317 A1* 12/2008 Shekhar et al. ............... 382/131
2009/0062641 A1 3/2009 Barbu et al.
2009/0163800 A1* 6/2009 Xu et al. ........................ 600/424
2009/0279767 A1 11/2009 Kukuk et al.
2010/0121181 A1 5/2010 Wang et al.
2012/0069003 A1 3/2012 Birkbeck et al.
2012/0070046 A1 3/2012 Wu et al.
2012/0232384 A1 9/2012 Wu et al.

* cited by examiner

METHOD AND SYSTEM FOR ABLATION CATHETER AND CIRCUMFERENTIAL MAPPING CATHETER TRACKING IN FLUOROSCOPIC IMAGES

This application claims the benefit of U.S. Provisional Application No. 61/536,102, filed Sep. 19, 2011, the disclosure of which is herein incorporated by reference.

BACKGROUND OF THE INVENTION

The present invention relates to detection and tracking of catheters in fluoroscopic images, and more particularly, to detecting and tracking an ablation catheter and a circumferential mapping catheter in fluoroscopic images to assist in atrial fibrillation ablation treatment.

Atrial fibrillation (AF) is a rapid, highly irregular heartbeat caused by abnormalities in the electrical signals generated by the atria of the heart. It is the most common cardiac arrhythmia (abnormal heart rhythm) and involves the two upper chambers (atria) of the heart. Surgical and catheter-based therapies have become common AF treatments throughout the world. Catheter ablation modifies the electrical pathways of the heart in order to treat AF. To measure electrical signals in the heart and assist the operation, different catheters are inserted into a patient's blood vessels and guided to the heart. The entire operation is monitored and guided with real-time fluoroscopic images. The integration of static tomographic volume renderings into three-dimensional catheter tracking systems has introduced an increased need for mapping accuracy during AF procedures. However, the heart is not a static structure, and the relative motion of mapping and reference catheters can lead to significant displacements. Current technologies typically concentrate on gating catheter position to a fixed point in time within the cardiac cycle based on an electrocardiogram (ECG), without compensating for respiration effects. The often advocated static positional reference provides an intermediate accuracy in association with ECG gating.

Tracking electrodes of a circumferential mapping catheter and/or an ablation catheter in fluoroscopic images can be used for real-time guidance and to compensate respiratory and cardiac motion for 3D overlay to assist physicians when positioning the ablation catheter. However, conventional tracking algorithms encounter difficulties in the presence of large image variations, nearby similar structures, and cluttered background.

BRIEF SUMMARY OF THE INVENTION

Embodiments of the present invention provide a robust and fast method to track electrodes of an ablation catheter (AC) and a circumferential mapping catheter (CMC) in a sequence of fluoroscopic images.

In one embodiment of the present invention, a catheter electrode models for one of an ablation catheter and a circumferential mapping catheter is initialized in a first frame of a fluoroscopic image sequence based on user inputs. The catheter model for the one of the ablation catheter and the circumferential mapping catheter is then tracked in a second frame of the fluoroscopic image sequence. Electrode candidates are detected in the second frame and tracking hypotheses for the catheter electrode model of the one of the ablation catheter and the circumferential mapping catheter are generated based on the catheter landmark candidates. The catheter landmarks for the ablation catheter may include ablation catheter electrodes and an ablation catheter tip, and the catheter landmarks for the circumferential mapping catheter may include circumferential mapping catheter electrodes and circumferential mapping catheter body points. A tracking hypothesis is selected as the catheter electrode model of the one of the ablation catheter and the circumferential mapping catheter in the second frame.

These and other advantages of the invention will be apparent to those of ordinary skill in the art by reference to the following detailed description and the accompanying drawings.

DETAILED DESCRIPTION

The present invention relates to a method and system for tracking an ablation catheter (AC) and a circumferential mapping catheter (CMC) in fluoroscopic images. Embodiments of the present invention are described herein to give a visual understanding of the AC and CMC tracking method. A digital image is often composed of digital representations of one or more objects (or shapes). The digital representation of an object is often described herein in terms of identifying and manipulating the object. Such manipulations are virtual manipulations accomplished in the memory or other circuitry/hardware of a computer system. Accordingly, is to be understood that embodiments of the present invention may be performed within a computer system using data stored within the computer system.

Figure 1:
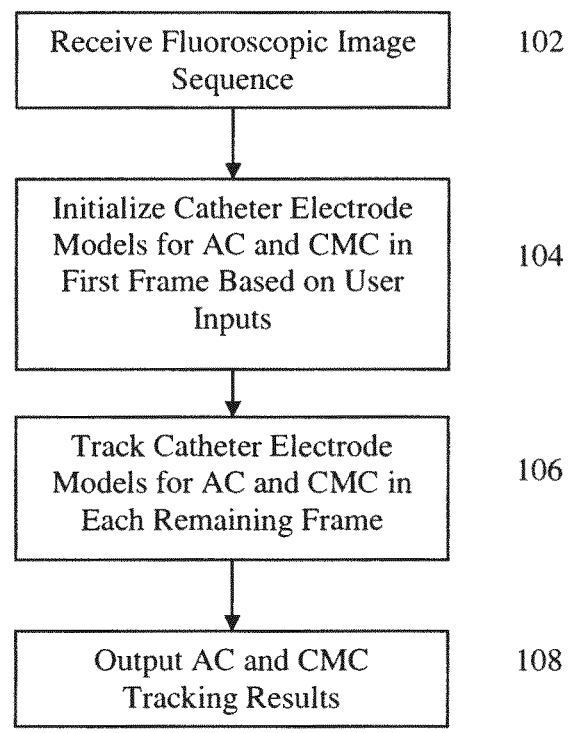
FIG. 1 illustrates a method for tracking an ablation catheter (AC) and a circumferential mapping catheter (CMC) in a sequence of fluoroscopic images.

FIG. 1 illustrates a method for tracking an ablation catheter (AC) and a circumferential mapping catheter (CMC) in a sequence of fluoroscopic images. As illustrated in FIG. 1, at step 102, a fluoroscopic image sequence is received. The fluoroscopic image sequence is a sequence of fluoroscopic (X-ray) images acquired over a time period. The fluoroscopic image sequence can be received directly from an x-ray imaging device. It is also possible that the fluoroscopic image sequence can be received by loading a previously stored fluoroscopic image sequence.

At step 104, catheter electrode models for the AC and the CMC are initialized in a first frame of the fluoroscopic image sequence based on user inputs. User inputs are received identifying locations of the AC electrodes and the CMC electrodes in the first frame of the fluoroscopic image sequence. In particular, using a computer input device, such as a mouse, a user can click on the locations of the AC electrodes and the locations of the CMC electrodes in the first frame of the fluoroscopic image sequence. Based on the received user input a respective catheter electrode model is generated and stored for the AC and the CMC.

Figure 2:
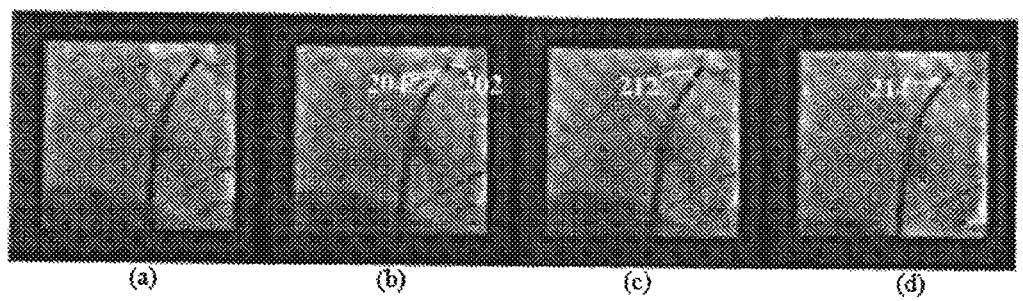
FIG. 2 illustrates ablation catheter initialization and detection in exemplary fluoroscopic images.

For the AC, user inputs can be received identifying the location of the ablation catheter tip and the locations of the ablation catheter electrodes. In an advantageous implementation, an ablation catheter tip and three ablation catheter electrodes are identified by the user inputs. FIG. 2 illustrates ablation catheter initialization and detection in exemplary fluoroscopic images. As illustrated in FIG. 2, image (a) shows an exemplary frame of a received fluoroscopic image sequence. Image (b) shows user input locations of the ablation catheter tip 202 and the ablation catheter electrodes 204. The user input locations of the catheter tip and ablation catheter electrodes are used to generate the ablation catheter template. In particular, an ablation catheter template is generated by storing the coordinates and the corresponding intensity values for each catheter electrode and the catheter tip input by a user in the first frame of the fluoroscopic image sequence by densely sampling points in normal directions along the spline constructed by the user input electrode locations (including the catheter tip). An electrode mask is also constructed for each part based on the relative locations of the electrodes (and the catheter tip). The electrode mask facilitates summing up electrode detection scores at individual electrode locations during tracking.

Figure 3:
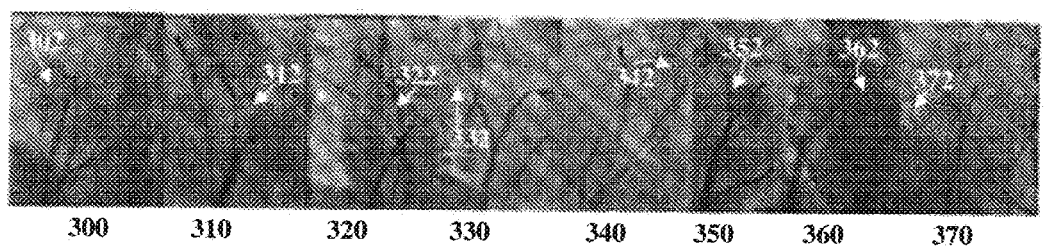
FIG. 3 illustrates exemplary circumferential mapping catheters in fluoroscopic images.

For the CMC, the electrodes of the CMC typically appear as an elliptical shape in fluoroscopic images. A plurality of CMC electrode locations in the first frame of the fluoroscopic image sequence can be input by a user. In an advantageous embodiment, at least six CMC electrode locations are received as user inputs. FIG. 3 illustrates exemplary circumferential mapping catheters in fluoroscopic images. As illustrated in FIG. 3 CMC catheters 302, 312, 322, 332, 342, 352, 362, and 372 are shown in fluoroscopic images 300, 310, 320, 330, 340, 350, 360, and 370, respectively. It can be seen that CMOs demonstrate various appearance and shapes in different contexts. The CMC catheter electrode model may be initialized by storing a template including the locations of the user input catheter electrodes of the CMC and/or parameters of an ellipse which mathematically approximates the input catheter electrode locations.

Returning to FIG. 1, at step 106, the catheter electrode models for the AC and the CMC are tracked in each remaining frame of the fluoroscopic image sequence. Each catheter electrode model (AC and CMC) is independently tracked in each frame by detecting catheter landmark candidates using learning-based catheter landmark detectors, generating tracking hypotheses for the catheter electrode model based on the catheter landmark candidates, and evaluating the tracking hypotheses to select the best tracking hypothesis to detect the catheter electrode model location, and thus the location of the catheter electrodes in each frame. For the AC, the catheter landmarks are the electrodes and the ablation catheter tip. For the CMC, the catheter landmarks are the electrodes and CMC body points.

Figure 4:
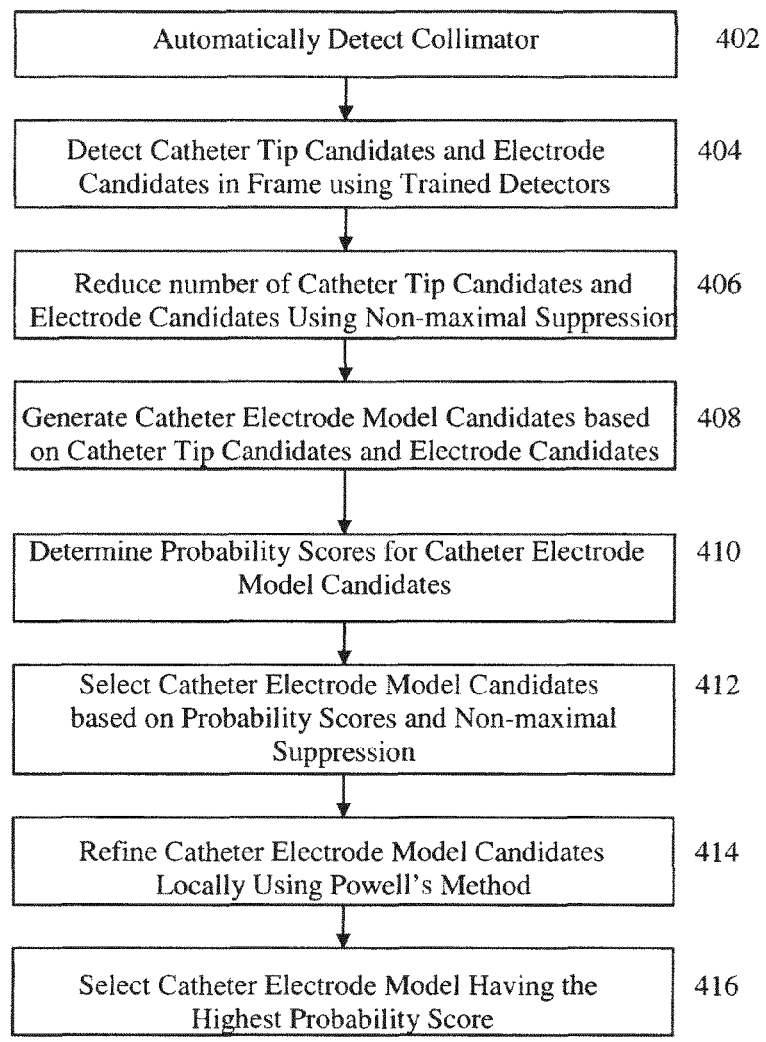
FIG. 4 illustrates a method for tracking the ablation catheter in a frame of a fluoroscopic image sequence according to an embodiment of the present invention.

FIG. 4 illustrates a method for tracking the ablation catheter in a frame of a fluoroscopic image sequence according to an embodiment of the present invention. The method of FIG. 4 can be repeated for each remaining frame of the fluoroscopic image sequence to implement step 106 of FIG. 1 for the AC. As illustrated in FIG. 4, at step 402, a collimator is automatically detected. The collimator is a black border of a fluoroscopic image. The collimator can be automatically detected using a trained border detector. The trained border detector can be trained using a machine-learning algorithm based on annotated training data. The location of the collimator is detected and stored. This allows the method to recognize cases in which the catheter electrode model for the AC is obscured by the collimator At step 404, catheter tip candidates and electrode candidates are detected in a frame of the fluoroscopic image sequence using trained detectors. Electrode (and catheter tip) detection can be formulated as an object detection framework to solve a two-class (object vs. background) classification problem. A box is used to scan the image to extract candidate samples. Each sample is fed to the trained electrode detector to obtain a probability score of being an AC electrode. For individual electrodes, the location parameter space has two parameters, x and y. According to an advantageous implementation, a box based representation is used, in which a box (e.g., 69×69 pixels) is centered at a candidate sample, in order to include both electrodes and their context.

According to an embodiment of the present invention, a probabilistic boosting tree (PBT) can be used as the core machine learning algorithm to train the electrode detector. The detector is a tree-based structure with which the posterior probabilities of the presence of the electrodes are calculated from given image data. Accordingly, the trained electrode detector not only provides a binary decision for a given sample but also a confidence value associated with the decision. The nodes of in the tree are constructed by a non-linear combination of simple classifiers using boosting techniques.

Figure 5:
FIG. 5 illustrates exemplary Haar wavelet-like features.

Each electrode detector selects a set of discriminative features that are used to distinguish the positive (electrode) locations from the negatives (background and other structures) from a large pool of features. Different parameter space utilizes different features calculated from image data. For individual electrode detectors, Haar wavelet-like features can be used. FIG. 5 illustrates exemplary Haar wavelet-like features.

According to an advantageous implementation, the electrode (and catheter tip) detection may be performed using multiple trained electrode detectors. For example, a bootstrapping strategy can be used to effectively remove false positive detections. In this case, there are two stages of trained detectors for individual electrode detection. The first stage detector is trained using annotated training data with target electrodes used as positive training samples and randomly selected negative training samples. The second stage detector is trained using the target electrodes as the positive training samples and false positives detected by the first stage detector as negative training samples. The first stage is used to quickly remove negative samples and the second stage is aimed at pruning out more confusing or difficult samples that may result in false positives. After detection using the first and second stage detectors, the detection results can be clustered into electrode candidate locations using non-maximal suppression. It is to be understood that a separate trained classifiers may be used to detect the catheter tip candidates and the candidate locations for the actual electrodes.

At step 406, the number of catheter tip candidates and electrode candidates is reduced using non-maximal suppression. Non-maximal suppression is a well-known technique that can be used to cluster detection results. This combines multiple candidates that are close together and should be considered as the same candidate. Referring to FIG. 2, image (c) of FIG. 2 shows automatically detected ablation catheter tip candidates 212 and image (d) of FIG. 2 shows automatically detected ablation catheter electrode candidates 214 detected using a trained PBT-based electrode detector, after non-maximal suppression.

Returning to FIG. 4, at step 408, catheter electrode model candidates for the AC are generated based on the electrode candidate positions detected in step 406. In a particular frame, steps 404 and 406 results in $K_1$ catheter tip candidates and $K_2$ electrode candidates after non-maximal suppression. For each of $K_1$ catheter tip candidates, a hypothesis is generated by translating the catheter tip of the catheter electrode model to that candidate location. For each of the $K_2$ electrode candidates, $K_2*(E-0)$ hypotheses are generated by translating each electrode (other than the catheter tip) in the catheter electrode model to that electrode candidate location. E is the total number of electrodes (including the catheter tip) in the catheter electrode model initialized in the first frame of the fluoroscopic image sequence. For example, in the embodiment in which the catheter electrode model includes the AC tip and three other AC electrodes, E=4. By performing these translations, $K_1+K_2*(E-1)$ catheter electrode model hypotheses are generated. For each catheter electrode model hypothesis, affine transformation is applied to the model by varying the translation, scale, rotation, and skew to obtain a set of candidate models. This results in a large number of catheter electrode model candidates (tracking hypotheses), each of which is a complete set of coordinates corresponding to locations of all of template points in the catheter electrode model.

At step 410, a probability score is determined for each of the electrode model candidates. The probability score is based on a comparison of the intensity values of the electrodes in the catheter electrode model hypothesis and the electrode model initialized in the first frame, as well as the detection scores for the electrodes in the model hypothesis using the trained electrode detector (or trained catheter tip detector). In particular, the probability (confidence) score for each catheter electrode model candidate can be expressed as:

$$P(C|M_i) = P_{Img}(C|M_i) \cdot P_{Det}(C|M_i)$$

where C denotes the ablation catheter and $M_i$ denotes the i-th candidate model. $P_{Img}(C|M_i)$ is the matching score given image intensity evidence and computed by normalized cross correlation between the intensity values of the template points in the candidate model and the intensity values of the template points in the electrode model initialized in the first frame. $P_{Det}(C|M_i)$ represents the probability value given by tip and electrode detection scores for the tip and electrode locations in the candidate model. The stored electrode mask for the initialized electrode model can be placed on the current frame using the affine parameters of the current candidate model. The trained tip detector and the trained electrode detector can then calculate the probability of the tip location in the candidate model being the ablation catheter tip and the probability of each electrode location being an electrode given by the electrode mask. The probabilities of the tip location and each electrode location for the candidate model can be summed to calculate $P_{Det}(C|M_i)$.

Alternatively, the probability (confidence) score for each catheter electrode model candidate can also be expressed as:

$$P(C|M_i) = (1-a) \cdot P_{Img}(C|M_i) + a \cdot P_{Det}(C|M_i)$$

where a is a weight whose value is between 0 and 1, and it can also be defined as $a=1/(1+e^{-P_{Img}(C|M_i)})$. Both score calculations shown in above equations have been implemented by the present inventors and are effective.

At step 412, a number of catheter electrode model candidates are selected having the highest probability scores. For example, a predetermined number of electrode model candidates having the highest probability scores may be selected. Alternatively, all catheter electrode model candidates having a probability score over a certain threshold may be selected. It is also possible that a predetermined number of catheter electrode model candidates having the highest probability scores over a certain threshold are selected. In an advantageous implementation, non-maximal suppression can be used to reduce the number of catheter electrode model candidates prior to selecting the catheter electrode model candidates having the highest scores.

At step 414, the selected electrode model candidates are refined to find the local maximum probability score for each candidate. In order to refine matching locally, Powell's method can be applied to find the local maximum probability score. Powell's method utilizes a bidirectional search along a search vector for each affine parameter in turn to maximize a candidate model's probability score. This is repeated a certain number of times or until the method converges and no further improvement is possible. This can achieve minor adjustments in the affine parameters of a candidate model that result in an improved probability score.

Figure 6:
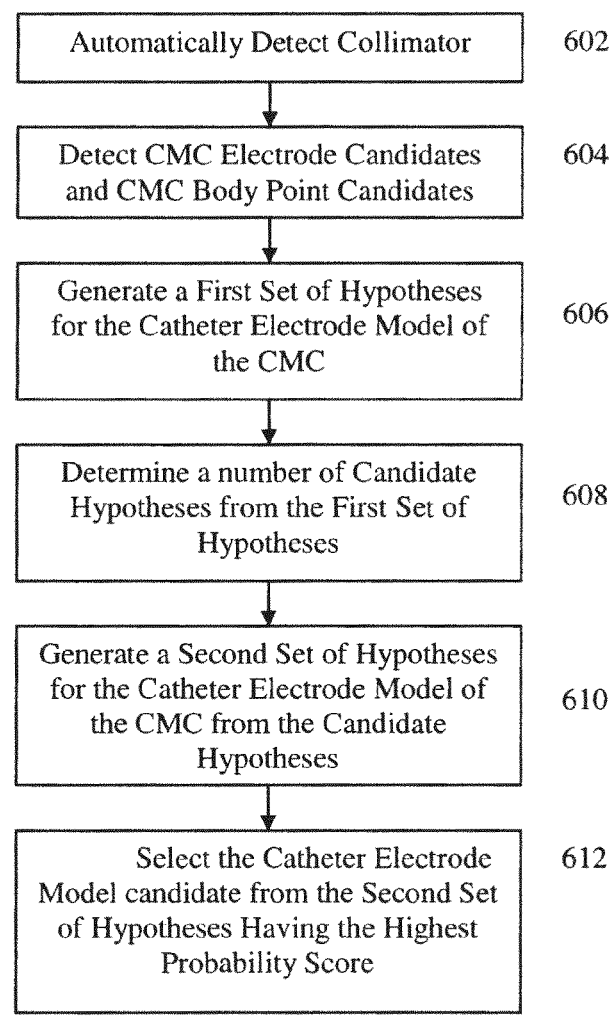
FIG. 6 illustrates a method for tracking the circumferential mapping catheter in a frame of a fluoroscopic image sequence according to an embodiment of the present invention.

At step 416, a catheter electrode model is detected in the frame by selecting the catheter electrode model candidate having the highest probability score. This catheter electrode model candidate gives the locations of all of the electrodes in the frame FIG. 6 illustrates a method for tracking the circumferential mapping catheter in a frame of a fluoroscopic image sequence according to an embodiment of the present invention. The method of FIG. 6 can be repeated for each remaining frame of the fluoroscopic image sequence to implement step 106 of FIG. 1 for the CMC. As illustrated in FIG. 6, at step 602, a collimator is automatically detected. The collimator is a black border of a fluoroscopic image. The collimator can be automatically detected using a trained border detector. The trained border detector can be trained using a machine-learning algorithm based on annotated training data. The location of the collimator is detected and stored. This allows the method to recognize cases in which the catheter electrode model for the CMC is obscured by the collimator.

At step 604, CMC electrode candidates and CMC body point candidates are detected in the current frame using respective trained detectors. In particular, trained detectors to detect CMC electrode candidates and CMC body points are trained by learning respective discriminative models based on appearance and contextual features of the CMC electrodes and body points, respectively, using annotated training data.

Accurate detection of CMC electrode candidates and body point candidates not only provides robust estimation of the catheter position, but also helps prune the search space for tracking the CMC. The CMC electrode candidates and CMC body point candidates are detected as points (x,y), parameterized by their position, which is detected using respective trained binary classifiers. In one implementation, the trained classifiers each use about 55,000 Haar features centered in a window of size $W_x \times W_y$ pixels (e.g., 35×35), but the present invention is not limited thereto. Each classifier can be a probabilistic boosting tree (PBT) trained from annotated training data, and each classifier can output a probability $P(d=(x,y)|D)$ for each point in the image.

2D X-ray fluoroscopy of AF procedures often consist of different devices and structures which can occlude the CMC during its movement or disturb detection of the CMC. In order to overcome this challenging problem, negative samples (non-CMC structures) can be detected in the first frame of the fluoroscopic image sequence using a trained CMC body detector. Based on the observation that most non-lasso (non-CMC) structures remain relatively static or exhibit little motion during AF procedures, the locations of the non-CMC structures detected in the first frame can be applied to the current frame in which the CMC is being tracked in order assist in evaluation of tracking hypotheses generated in the current frame for the catheter model of the CMC.

Figure 7:
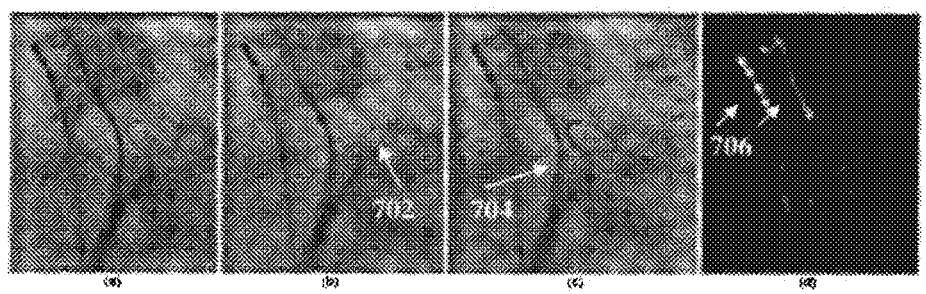
FIG. 7 illustrates exemplary results of CMC electrode and body point candidate detection.

FIG. 7 illustrates exemplary results of CMC electrode and body point candidate detection. As shown in FIG. 7, image (a) shows an input image. Image (b) shows automatically detected CMC electrode candidates 702 after non-maximal suppression. Image (c) shows automatically detected CMC body point candidates 704. Image (d) shows the detected non-CMC structures 706

Returning to FIG. 6, at step 606, a first set of hypotheses are generated for the catheter electrode model of the CMC bases on the detected CMC electrode candidates. In particular, given the CMC model $C_0$ initialized in the first frame and the set of detected electrode candidate locations $B_t$, a set of seed hypotheses is generate by translating each of the electrodes in initialized CMC model $C_0$ to each detected electrode candidate location in $B_t$. That is, in frame t, each electrode $e^i$ in $C_0$ is translated to each electrode candidate location $b^j$ in $B_t$ to obtain a seed hypothesis $\bar{h}_t^{ij}$ and its associated model center $m_t^{ij}$. The seed hypothesis is the ellipse shape of the initialized model. Since the tracking hypotheses are generated in the way that the algorithm could only miss the ground truth if none of the electrodes along the CMC are detected, the probability of missing the ground truth hypothesis is significantly low.

At step 608, a set of candidate hypotheses are detected from the first set of hypotheses for the catheter electrode model of the CMC. After the first set of hypotheses are generated, the first set of hypotheses are evaluated after first applying the Powell's method on the generated seed hypotheses to detect density surfaces to search for a maximum probability hypothesis. Powell's method utilizes a bidirectional search along a search vector for each affine parameter in turn to maximize a candidate model's probability score. This is repeated a certain number of times or until the method converges and no further improvement is possible. This can achieve minor adjustments in the affine parameters of a candidate model that result in an improved probability score An effective hypothesis evaluation is necessary to determine the exact position and shape of the CMC. According to an advantageous embodiment of the present invention, a Bayesian framework is used to evaluate the CMC tracking hypotheses. The goal for evaluating a tracking hypothesis is to maximize the posterior probability: $\hat{h}_t = \arg\max_{h_t} P(h_t | Z_{0...t})$, where $Z_{0...t}$ is an image observation from the 0 to the t-th frame. By assuming a Markovian representation of the CMC motion, the formula can be expanded as:

$$\hat{h}_t = \underset{h_t}{\operatorname{argmax}} P(Z_t | h_t) P(h_t | h_{t-1}) P(h_{t-1} | Z_{0...t-1}). \quad (1)$$

Figure 8:
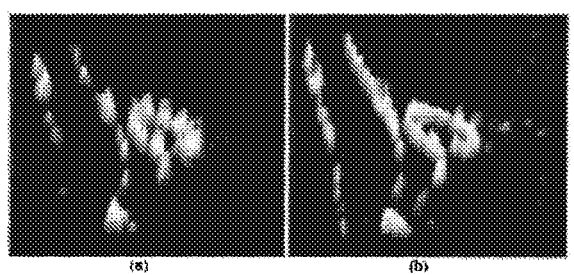
FIG. 8 illustrates exemplary CMC electrode (image (a)) and body point (image (b)) probability maps.

The formula in Equation (1) essentially combines two parts: a likelihood term, $P(Z_t|h_t)$, which is calculated as detection probability, and a prediction term $P(h_t|h_{t-1})$, which captures the motion smoothness. To maximize tracking robustness, the likelihood term $P(Z_t|h_t)$ is estimated by combining the CMC electrode and body detection probability as follows:

$$P(Z_t|h_t) = P(C_t^*|h_t), \quad (2)$$

where $C_t^*$ is the estimated detection probability at the t-th frame that assists estimation of $h_t$ and the detection term $P(C_t^*|h_t)$ is defined in terms of a part model as:

$$P(C_t^* | h_t) = \frac{1}{K}\sum_{i=1}^{K} P(E_t^* | h_t^i) + \frac{1}{N}\sum_{i=1}^{N} P(B_t^* | h_t^i) - \beta P(C_- | h_t^i), \quad (3)$$

where $P(E_t^*|h_t^i)$ represents the CMC electrode detection probability, $P(B_t^*|h_t^i)$ represents the body point detection probability and $P(C_-|h_t^i)$ represents the non-CMC probability learned from the initial frame. FIG. 8 illustrates exemplary CMC electrode (image (a)) and body point (image (b)) probability maps.

A set of top hypotheses (having the highest probability score) from the first set of hypotheses can be clustered using a non-maximal suppression algorithm. The algorithm first sorts all of the hypotheses by their probability or confidence scores. The algorithm then adds the top hypothesis (having the highest probability score) into a target list. For the next top hypothesis, the algorithm checks if it the hypothesis is similar or close to any in the target list. The algorithm evaluates the similarity based on translation and rotation parameters. If the hypothesis is not similar (evaluated parametrically) to a hypothesis already in the target list, it is added to the target list. When the number of hypotheses in the target list reaches a threshold, the non-maximal suppression algorithm stops. This algorithm results in a set of candidate hypotheses, $S_t$:$s_t^i$.

At step 610, a second set of hypotheses for the catheter model of the CMC are generated from the candidate hypotheses $S_t$. Applying Powell's method on the generated seed hypotheses in the detection density surface may lead to a local-minimum solution. Accordingly, in an advantageous embodiment of the present invention a second stage of hypothesis searching is performed on the top candidates determined for the first set of hypotheses. In particular, for each candidate hypothesis $s_t^i$, multiple CMC tracking hypotheses are generated by translating $s_t^i$ by $(u_x, u_y)$ where $u_x \in \{-\rho, 0, \rho\}$, $u_y \in \{-\rho, 0, \rho\}$ and $\|u_x\| = \|u_y\|$ where $\rho$ is a scale step size. Thus, this translation leads to five new positions for each candidate hypothesis $S_t^i$. At each new position, either the x or y scale is increased by a step or both the x and y scales are increased by a step. The scale step $\rho$ for x or y can be calculated based on the CMC model's long axis and short axis lengths. In a possible implementation, the hypothesis generation can be repeated at multiple scales for each candidate hypothesis $S_t^i$. For example, the hypothesis generation can be performed at three scale steps for each candidate $S_t^i$ hypothesis, resulting in 15 second stage hypotheses being generated for each candidate hypothesis $S_t^i$. The rationale of increasing the scale parameters instead of decreasing the scale parameters is based on the observation by the present inventors that the CMC is an ellipse-like line structure and the local-minimum solution of Powell's method typically under-fits the ground truth in size.

At step 612, a catheter electrode model for the CMC is selected from the second set of hypotheses. Powell's method can be performed each CMC tracking hypothesis in the second set of hypotheses and then the second set of hypotheses can be evaluated as described above in step 608 to determine a probability score for each tracking hypothesis. The tracking hypothesis having the highest probability score is selected as the electrode model of the CMC in the current frame.

Returning to FIG. 1, at step 108, the AC and CMC tracking results for each frame of the fluoroscopic image sequence are output. For example, the tracked catheter electrode models for the AC and the CMC in each frame of the fluoroscopic image sequence can be displayed on a display of a computer system.

Although the method of FIG. 1 describes that both the AC and CMC are tracked in each frame of the fluoroscopic image sequence, it is possible that only one of the AC and CMC can be tracked using the methods described above.

Figure 9:
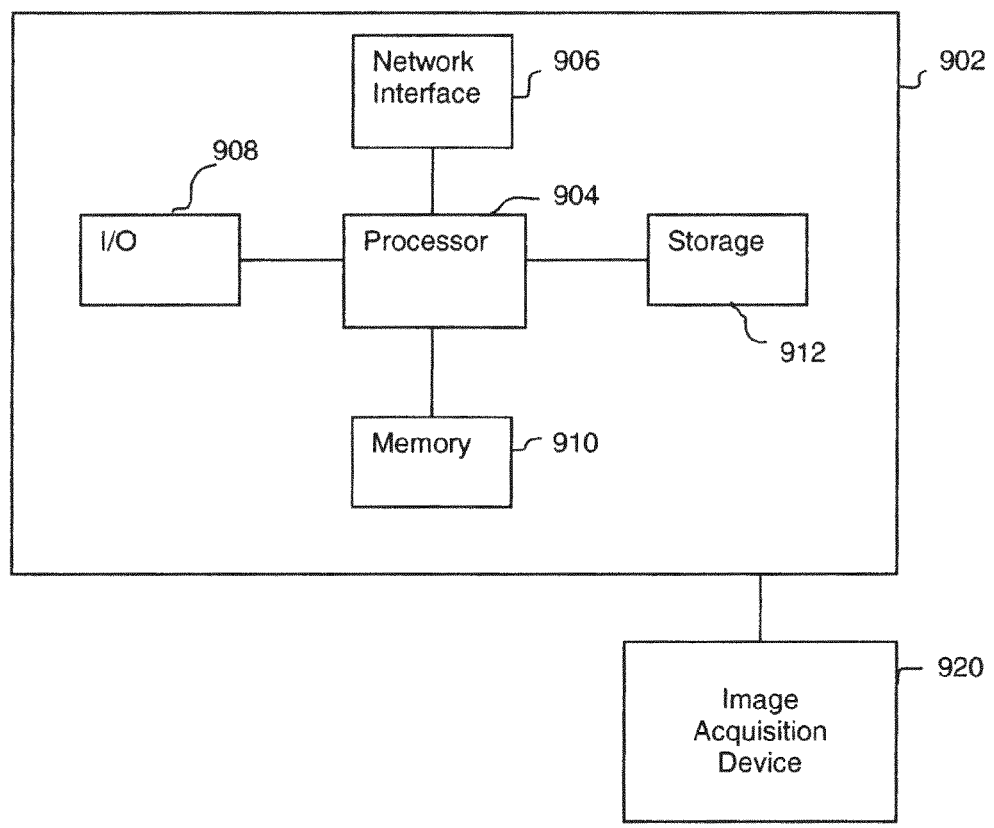
FIG. 9 is a high level block diagram of a computer capable of implementing the present invention.

The above-described methods for ablation catheter and circumferential mapping catheter tracking in a fluoroscopic image sequence may be implemented on a computer using well-known computer processors, memory units, storage devices, computer software, and other components. A high level block diagram of such a computer is illustrated in FIG. 9. Computer 902 contains a processor 904 which controls the overall operation of the computer 902 by executing computer program instructions which define such operation. The computer program instructions may be stored in a storage device 912, or other computer readable medium, (e.g., magnetic disk) and loaded into memory 910 when execution of the computer program instructions is desired. Thus, all method steps described above, including the method steps illustrated in FIGS. 1, 4, and 6 may be defined by the computer program instructions stored in the memory 910 and/or storage 912 and controlled by the processor 904 executing the computer program instructions. An image acquisition device 920, such as an X-ray imaging device, can be connected to the computer 902 to input fluoroscopic image sequences to the computer 902. It is possible to implement the image acquisition device 920 and the computer 902 as one device. It is also possible that the image acquisition device 920 and the computer 902 communicate wirelessly through a network. The computer 902 also includes one or more network interfaces 906 for communicating with other devices via a network. The computer 902 also includes other input/output devices 908 that enable user interaction with the computer 902 (e.g., display, keyboard, mouse, speakers, buttons, etc.) One skilled in the art will recognize that an implementation of an actual computer could contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for tracking at least one of an ablation catheter and a circumferential mapping catheter in a fluoroscopic image sequence, comprising:
   initializing a catheter electrode model of one of an ablation catheter and a circumferential mapping catheter in a first frame of a fluoroscopic image sequence based on input locations of a plurality of electrodes of the one of the ablation catheter and the circumferential mapping catheter in the first frame, wherein the catheter electrode model in the first frame comprises a plurality of template points corresponding to locations of the electrodes of the one of the ablation catheter and the circumferential mapping catheter in the first frame; and
   tracking the catheter electrode model of the one of the ablation catheter and the circumferential mapping catheter in a second frame of the fluoroscopic image sequence by:
      detecting catheter landmark candidates in a second frame of the fluoroscopic image sequence using at least one trained catheter landmark detector, wherein the catheter landmark candidates include electrode candidates;
      generating a plurality of tracking hypotheses for the catheter electrode model of the one of the ablation catheter and the circumferential mapping catheter in the second frame based on the detected catheter landmark candidates and the catheter electrode model initialized in the first frame by translating each of the plurality of template points of the catheter electrode model initialized in the first frame to each of the detected electrode candidates in the second frame; and
      selecting one of the tracking hypotheses as the catheter electrode model of the one of the ablation catheter and the circumferential mapping catheter in the second frame, wherein the selected tracking hypothesis defines the catheter electrode model; wherein the catheter electrode model provides locations of the plurality of electrodes of the one of the ablation catheter and the circumferential mapping catheter in the second frame.

2. The method of claim 1, wherein the one of the ablation catheter and circumferential mapping catheter comprises the ablation catheter and the step of initializing a catheter electrode model of one of an ablation catheter and a circumferential mapping catheter in a first frame of a fluoroscopic image sequence based on input locations of a plurality of electrodes of the one of the ablation catheter and the circumferential mapping catheter in the first frame comprises:
   initializing a catheter electrode model of the ablation catheter based on input ablation catheter electrode locations and an input ablation catheter tip location.

3. The method of claim 2, wherein the step of detecting catheter landmark candidates in a second frame of the fluoroscopic image sequence using at least one trained catheter landmark detector comprises:
   detecting ablation catheter electrode candidates in the second frame using a trained electrode detector; and
   detecting ablation catheter tip candidates in the second frame using a trained catheter tip detector.

4. The method of claim 3, wherein the step of generating a plurality of tracking hypotheses for the catheter electrode model of the one of the ablation catheter and the circumferential mapping catheter in the second frame based on the detected catheter landmark candidates and the catheter electrode model initialized in the first frame by translating each of the plurality of template points of the catheter electrode model initialized in the first frame to each of the detected electrode candidates in the second frame comprises:
   generating a first plurality of hypotheses for the catheter electrode model of the ablation catheter by translating a catheter tip of the catheter electrode model of the ablation catheter initialized in the first frame to each of the detected ablation catheter tip candidates in the second frame;
   generating a second plurality of hypotheses for the catheter electrode model of the ablation catheter by translating each of a plurality of electrodes of the catheter electrode model of the ablation catheter initialized in the first frame to each detected ablation catheter electrode candidate in the second frame; and
   generating multiple tracking hypotheses from each hypothesis of the first and second plurality of hypotheses for the catheter electrode model of the ablation catheter by varying affine parameters of each hypothesis.

5. The method of claim 4, wherein the step of selecting one of the tracking hypotheses as the catheter electrode model of the one of the ablation catheter and the circumferential mapping catheter in the second frame comprises:

calculating a probability score for each of the tracking hypotheses for the catheter electrode model of the ablation catheter;

selecting a number of electrode model candidates having highest probability scores from the plurality of tracking hypotheses;

refining affine parameters of the selected electrode model candidates to locally maximize the probability scores; and selecting the electrode model candidate having the highest locally maximized probability score.

6. The method of claim 5, wherein the step of calculating a probability score for each of the tracking hypotheses for the catheter electrode model of the ablation catheter comprises:

calculating a probability score as based on a first probability score and a second probability score, wherein the first probability score is calculated by normalized cross correlation between intensity values of the template points in the second frame identified by the respective tracking hypothesis and the intensity values of the template points in the first frame identified by the catheter electrode model of the ablation catheter initialized in the first frame, and the second probability score is calculated based on detection scores of electrodes identified by the respective tracking hypothesis determined by the trained electrode detector, wherein the electrodes identified by the respective tracking hypothesis are identified in the second frame using an electrode mask derived from the template points in the first frame.

7. The method of claim 1, wherein the one of the ablation catheter and the circumferential mapping catheter comprises the circumferential mapping catheter and the step of initializing a catheter electrode model of one of an ablation catheter and a circumferential mapping catheter in a first frame of a fluoroscopic image sequence based on input locations of a plurality of electrodes of the one of the ablation catheter and the circumferential mapping catheter in the first frame comprises:

receiving user input locations of a plurality of circumferential mapping catheter electrodes in the first frame; and determining an ellipse that mathematically approximates the input plurality of circumferential mapping catheter electrodes in the first frame.

8. The method of claim 7, wherein the step of detecting catheter landmark candidates in a second frame of the fluoroscopic image sequence using at least one trained catheter landmark detector comprises:

detecting circumferential mapping catheter electrode candidates in the second frame using a trained electrode detector; and detecting circumferential mapping catheter body point candidates in the second frame using a trained body point detector.

9. The method of claim 8, wherein the step of detecting catheter landmark candidates in a second frame of the fluoroscopic image sequence using at least one trained catheter landmark detector further comprises:

detecting non-circumferential mapping catheter structures in the first frame using a trained detector; and applying the non-circumferential mapping catheter structures detected in the first frame to the second frame.

10. The method of claim 8, wherein the step of generating a plurality of tracking hypotheses for the catheter electrode model of the one of the ablation catheter and the circumferential mapping catheter in the second frame based on the detected catheter landmark candidates and the catheter electrode model initialized in the first frame by translating each of the plurality of template points of the catheter electrode model initialized in the first frame to each of the detected electrode candidates in the second frame comprises:

generating a first set of tracking hypotheses for the catheter electrode model of the circumferential mapping catheter by translating each of the plurality of circumferential mapping catheter electrodes in the catheter model initialized in the first frame to each detected circumferential mapping catheter electrode candidate in the second frame.

11. The method of claim 10, wherein the step of generating a plurality of tracking hypotheses for the catheter electrode model of the one of the ablation catheter and the circumferential mapping catheter in the second frame based on the detected catheter landmark candidates and the catheter electrode model initialized in the first frame by translating each of the plurality of template points of the catheter electrode model initialized in the first frame to each of the detected electrode candidates in the second frame further comprises:

calculating a probability score for each hypothesis in the first set of tracking hypotheses;

selecting a number of candidate hypotheses having highest probability scores from the first set of hypotheses; and generating a second set of tracking hypotheses from the candidate hypotheses.

12. The method of claim 11, wherein the step of calculating a probability score for each hypothesis in the first set of tracking hypotheses comprises:

calculating a probability score for each hypothesis in the first set of tracking hypotheses based on a likelihood term and a prediction term, wherein the likelihood term is based on detection probabilities of circumferential mapping catheter electrodes and circumferential mapping catheter body points on the catheter electrode model defined by the hypothesis.

13. The method of claim 11, wherein the step of generating a second set of tracking hypotheses from the candidate hypotheses comprises:

generating a plurality of tracking hypotheses for each candidate hypothesis by translating each candidate hypothesis to five new positions and then changing at least one scale step in at least one of the x or y directions in the second frame at each new position.

14. The method of claim 11, wherein the step of selecting one of the tracking hypotheses as the catheter electrode model of the one of the ablation catheter and the circumferential mapping catheter in the second frame comprises:

calculating the probability score for each of the second set of tracking hypotheses; and selecting a tracking hypothesis having the highest probability score from the second set of tracking hypotheses as the catheter electrode model of the circumferential mapping catheter in the second frame.

15. An apparatus for tracking at least one of an ablation catheter and a circumferential mapping catheter in a fluoroscopic image sequence, comprising:

means for initializing a catheter electrode model of one of an ablation catheter and a circumferential mapping catheter in a first frame of a fluoroscopic image sequence based on input locations of a plurality of electrodes of the one of the ablation catheter and the circumferential mapping catheter in the first frame, wherein the catheter electrode model in the first frame comprises a plurality of template points corresponding to locations of the electrodes of the one of the ablation catheter and the circumferential mapping catheter in the first frame; and means for tracking the catheter electrode model of the one of the ablation catheter and the circumferential mapping catheter in a second frame of the fluoroscopic image sequence, comprising:
- means for detecting catheter landmark candidates in a second frame of the fluoroscopic image sequence using at least one trained catheter landmark detector, wherein the catheter landmark candidates include electrode candidates;
- means for generating a plurality of tracking hypotheses for the catheter electrode model of the one of the ablation catheter and the circumferential mapping catheter in the second frame based on the detected catheter landmark candidates and the catheter electrode model initialized in the first frame by translating each of the plurality of template points of the catheter electrode model initialized in the first frame to each of the detected electrode candidates in the second frame; and
- means for selecting one of the tracking hypotheses as the catheter electrode model of the one of the ablation catheter and the circumferential mapping catheter in the second frame, wherein the selected tracking hypothesis defines the catheter electrode model; wherein the catheter electrode model provides locations of the plurality of electrodes of the one of the ablation catheter and the circumferential mapping catheter in the second frame.

16. The apparatus of claim 15, wherein the one of the ablation catheter and circumferential mapping catheter comprises the ablation catheter and means for detecting catheter landmark candidates in a second frame of the fluoroscopic image sequence using at least one trained catheter landmark detector comprises:
- means for detecting ablation catheter electrode candidates in the second frame using a trained electrode detector; and
- means for detecting ablation catheter tip candidates in the second frame using a trained catheter tip detector.

17. The apparatus of claim 16, wherein the means for generating a plurality of tracking hypotheses for the catheter electrode model of the one of the ablation catheter and the circumferential mapping catheter in the second frame based on the detected catheter landmark candidates and the catheter electrode model initialized in the first frame by translating each of the plurality of template points of the catheter electrode model initialized in the first frame to each of the detected electrode candidates in the second frame comprises:
- means for generating a first plurality of hypotheses for the catheter electrode model of the ablation catheter by translating a catheter tip of the catheter electrode model of the ablation catheter initialized in the first frame to each of the detected ablation catheter tip candidates in the second frame;
- means for generating a second plurality of hypotheses for the catheter electrode model of the ablation catheter by translating each of a plurality of electrodes of the catheter electrode model of the ablation catheter initialized in the first frame to each detected ablation catheter electrode candidate in the second frame; and
- means for generating multiple tracking hypotheses from each hypothesis of the first and second plurality of hypotheses for the catheter electrode model of the ablation catheter by varying affine parameters of each hypothesis.

18. The apparatus of claim 17, wherein the means for selecting one of the tracking hypotheses as the catheter electrode model of the one of the ablation catheter and the circumferential mapping catheter in the second frame comprises:
- means for calculating a probability score for each of the tracking hypotheses for the catheter electrode model of the ablation catheter;
- means for selecting a number of electrode model candidates having highest probability scores from the plurality of tracking hypotheses;
- means for refining affine parameters of the selected electrode model candidates to locally maximize the probability scores; and
- means for selecting the electrode model candidate having the highest locally maximized probability score.

19. The apparatus of claim 15, wherein the one of the ablation catheter and the circumferential mapping catheter comprises the circumferential mapping catheter and the means for detecting catheter landmark candidates in a second frame of the fluoroscopic image sequence using at least one trained catheter landmark detector comprises:
- means for detecting circumferential mapping catheter electrode candidates in the second frame using a trained electrode detector; and
- means for detecting circumferential mapping catheter body point candidates in the second frame using a trained body point detector.

20. The apparatus of claim 19, wherein the means for generating a plurality of tracking hypotheses for the catheter electrode model of the one of the ablation catheter and the circumferential mapping catheter in the second frame based on the detected catheter landmark candidates and the catheter electrode model initialized in the first frame by translating each of the plurality of template points of the catheter electrode model initialized in the first frame to each of the detected electrode candidates in the second frame comprises:
- means for generating a first set of tracking hypotheses for the catheter electrode model of the circumferential mapping catheter by translating each of the plurality of circumferential mapping catheter electrodes in the catheter model initialized in the first frame to each detected circumferential mapping catheter electrode candidate in the second frame.

21. The apparatus of claim 20, wherein the means for generating a plurality of tracking hypotheses for the catheter electrode model of the one of the ablation catheter and the circumferential mapping catheter in the second frame based on the detected catheter landmark candidates and the catheter electrode model initialized in the first frame by translating each of the plurality of template points of the catheter electrode model initialized in the first frame to each of the detected electrode candidates in the second frame further comprises:
- means for calculating a probability score for each hypothesis in the first set of tracking hypotheses;
- means for selecting a number of candidate hypotheses having highest probability scores from the first set of hypotheses; and
- means for generating a second set of tracking hypotheses from the candidate hypotheses.

22. The apparatus of claim 21, wherein the means for selecting one of the tracking hypotheses as the catheter electrode model of the one of the ablation catheter and the circumferential mapping catheter in the second frame comprises:
- means for calculating the probability score for each of the second set of tracking hypotheses; and means for selecting a tracking hypothesis having the highest probability score from the second set of tracking hypotheses as the catheter electrode model of the circumferential mapping catheter in the second frame.

23. A non-transitory computer readable medium storing computer program instructions for tracking at least one of an ablation catheter and a circumferential mapping catheter in a fluoroscopic image sequence, wherein the computer program instructions, when executed on a processor, cause the processor to perform operations comprising:

initializing a catheter electrode model of one of an ablation catheter and a circumferential mapping catheter in a first frame of a fluoroscopic image sequence based on input locations of a plurality of electrodes of the one of the ablation catheter and the circumferential mapping catheter in the first frame, wherein the catheter electrode model in the first frame comprises a plurality of template points corresponding to locations of the electrodes of the one of the ablation catheter and the circumferential mapping catheter in the first frame; and tracking the catheter electrode model of the one of the ablation catheter and the circumferential mapping catheter in a second frame of the fluoroscopic image sequence by:

detecting catheter landmark candidates in a second frame of the fluoroscopic image sequence using at least one trained catheter landmark detector, wherein the catheter landmark candidates include electrode candidates;

generating a plurality of tracking hypotheses for the catheter electrode model of the one of the ablation catheter and the circumferential mapping catheter in the second frame based on the detected catheter landmark candidates and the catheter electrode model initialized in the first frame by translating each of the plurality of template points of the catheter electrode model initialized in the first frame to each of the detected electrode candidates in the second frame; and selecting one of the tracking hypotheses as the catheter electrode model of the one of the ablation catheter and the circumferential mapping catheter in the second frame, wherein the selected tracking hypothesis defines the catheter electrode model; wherein the catheter electrode model provides locations of the plurality of electrodes of the one of the ablation catheter and the circumferential mapping catheter in the second frame.

24. The non-transitory computer readable medium of claim 23, wherein the one of the ablation catheter and the circumferential mapping catheter comprises the ablation catheter and the operation of detecting catheter landmark candidates in a second frame of the fluoroscopic image sequence using at least one trained catheter landmark detector comprises:

detecting ablation catheter electrode candidates in the second frame using a trained electrode detector; and detecting ablation catheter tip candidates in the second frame using a trained catheter tip detector.

25. The non-transitory computer readable medium of claim 24, wherein the operation of generating a plurality of tracking hypotheses for the catheter electrode model of the one of the ablation catheter and the circumferential mapping catheter in the second frame based on the detected catheter landmark candidates and the catheter electrode model initialized in the first frame by translating each of the plurality of template points of the catheter electrode model initialized in the first frame to each of the detected electrode candidates in the second frame comprises:

generating a first plurality of hypotheses for the catheter electrode model of the ablation catheter by translating a catheter tip of the catheter electrode model of the ablation catheter initialized in the first frame to each of the detected ablation catheter tip candidates in the second frame;

generating a second plurality of hypotheses for the catheter electrode model of the ablation catheter by translating each of a plurality of electrodes of the catheter electrode model of the ablation catheter initialized in the first frame to each detected ablation catheter electrode candidate in the second frame; and generating multiple tracking hypotheses from each hypothesis of the first and second plurality of hypotheses for the catheter electrode model of the ablation catheter by varying affine parameters of each hypothesis.

26. The non-transitory computer readable medium of claim 25, wherein the operation of selecting one of the tracking hypotheses as the catheter electrode model of the one of the ablation catheter and the circumferential mapping catheter in the second frame comprises:

calculating a probability score for each of the tracking hypotheses for the catheter electrode model of the ablation catheter;

selecting a number of electrode model candidates having highest probability scores from the plurality of tracking hypotheses;

refining affine parameters of the selected electrode model candidates to locally maximize the probability scores; and selecting the electrode model candidate having the highest locally maximized probability score.

27. The non-transitory computer readable medium of claim 23, wherein the one of the ablation catheter and the circumferential mapping catheter comprises the circumferential mapping catheter and the operation of detecting catheter landmark candidates in a second frame of the fluoroscopic image sequence using at least one trained catheter landmark detector comprises:

detecting circumferential mapping catheter electrode candidates in the second frame using a trained electrode detector; and detecting circumferential mapping catheter body point candidates in the second frame using a trained body point detector.

28. The non-transitory computer readable medium of claim 27, wherein the operation of generating a plurality of tracking hypotheses for the catheter electrode model of the one of the ablation catheter and the circumferential mapping catheter in the second frame based on the detected catheter landmark candidates and the catheter electrode model initialized in the first frame by translating each of the plurality of template points of the catheter electrode model initialized in the first frame to each of the detected electrode candidates in the second frame comprises:

generating a first set of tracking hypotheses for the catheter electrode model of the circumferential mapping catheter by translating each of the plurality of circumferential mapping catheter electrodes in the catheter model initialized in the first frame to each detected circumferential mapping catheter electrode candidate in the second frame.

29. The non-transitory computer readable medium of claim 28, wherein the operation of generating a plurality of tracking hypotheses for the catheter electrode model of the one of the ablation catheter and the circumferential mapping catheter in the second frame based on the detected catheter landmark candidates and the catheter electrode model initialized in the first frame by translating each of the plurality of template points of the catheter electrode model initialized in the first frame to each of the detected electrode candidates in the second frame further comprises:
- calculating a probability score for each hypothesis in the first set of tracking hypotheses;
- selecting a number of candidate hypotheses having highest probability scores from the first set of hypotheses; and
- generating a second set of tracking hypotheses from the candidate hypotheses.

30. The non-transitory computer readable medium of claim 29, wherein the operation of selecting one of the tracking hypotheses as the catheter electrode model of the one of the ablation catheter and the circumferential mapping catheter in the second frame comprises:
- calculating the probability score for each of the second set of tracking hypotheses; and
- selecting a tracking hypothesis having the highest probability score from the second set of tracking hypotheses as the catheter electrode model of the circumferential mapping catheter in the second frame.

* * * * *